US011628030B2

(12) United States Patent
Thompson et al.

(10) Patent No.: US 11,628,030 B2
(45) Date of Patent: Apr. 18, 2023

(54) CONNECTION SYSTEMS AND METHODS THEREOF FOR ESTABLISHING AN ELECTRICAL CONNECTION THROUGH A DRAPE (71) Applicant: Bard Access Systems, Inc., Salt Lake City, UT (US)

(72) Inventors: Chase Thompson, Bountiful, UT (US); Kent F. Beck, Layton, UT (US); Jerry Zhao, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/723,246

(22) Filed: Apr. 18, 2022

(65) Prior Publication Data
US 2022/0241044 A1 Aug. 4, 2022

Related U.S. Application Data (63) Continuation of application No. 16/932,425, filed on Jul. 17, 2020, now Pat. No. 11,304,772, which is a
(Continued)

(51) Int. Cl.
*H01R 13/64* (2006.01)
*A61B 46/23* (2016.01)
*A61M 39/18* (2006.01)

(52) U.S. Cl.
CPC ............ *A61B 46/23* (2016.02); *A61M 39/18* (2013.01); *A61B 2046/234* (2016.02)

(58) Field of Classification Search
CPC ... A61B 46/23; A61B 2046/234; A61M 39/18
See application file for complete search history.

(56) References Cited

U.S. PATENT DOCUMENTS 2,831,174 A 4/1958 Hilmo
2,959,766 A 11/1960 Edwin
(Continued)

FOREIGN PATENT DOCUMENTS

EP 1318576 A1 6/2003
EP 3270817 A1 1/2018
(Continued)

OTHER PUBLICATIONS

"Sampling Accessories" Spectrometers Accessories Catalogue, pp. 71-102, XP055014465, retrieved from the Internet URL: http//www.mikropack.de/d/specto/pdfy-downoads/sampling accessories. pdf, Jan. 1, 2004 (Jan. 1, 2004).
(Continued)

*Primary Examiner* — Abdullah A Riyami
*Assistant Examiner* — Nelson R. Burgos-Guntin
(74) *Attorney, Agent, or Firm* — Rutan & Tucker LLP (57) ABSTRACT

Connection systems are disclosed for establishing one or more electrical connections through a drape. An example connection system includes a first connector and a second connector configured to connect to each other. The first connector includes a first-connector housing, an electrical lead extending from the first-connector housing, and at least a first piercing element within the first-connector housing configured to pierce the drape. The first piercing element is orthogonally connected to the electrical lead. The second connector includes a second-connector housing and at least a first receptacle within the second-connector housing. The first receptacle is configured to form at least a first electrical connection of the one or more electrical connections with the first piercing element when the first connector is disposed over the second connector with the drape therebetween. Methods are also disclosed herein for establishing
(Continued)

one or more electrical connections through a drape with the connection systems.

13 Claims, 6 Drawing Sheets

Related U.S. Application Data continuation of application No. 16/402,074, filed on May 2, 2019, now Pat. No. 10,772,696.

(60) Provisional application No. 62/673,726, filed on May 18, 2018.

(56) References Cited

U.S. PATENT DOCUMENTS

| | | | |
|---|---|---|---|
| 3,329,928 A | 7/1967 | Broske | |
| 3,532,095 A | 10/1970 | Miller et al. | |
| 3,597,582 A | 8/1971 | Goode et al. | |
| 3,605,743 A | 9/1971 | Arce | |
| 3,665,372 A | 5/1972 | Goode et al. | |
| 3,673,548 A | 6/1972 | Mattingly, Jr. et al. | |
| 3,746,814 A | 7/1973 | Lackey et al. | |
| 3,824,556 A | 7/1974 | Berkovits et al. | |
| 3,842,394 A | 10/1974 | Bolduc | |
| 4,200,348 A | 4/1980 | Stupay | |
| 4,220,387 A | 9/1980 | Biche et al. | |
| 4,254,764 A | 3/1981 | Neward | |
| 4,303,293 A | 12/1981 | Grunwald | |
| 4,369,794 A | 1/1983 | Furler | |
| 4,490,003 A | 12/1984 | Robinson | |
| 4,614,395 A | 9/1986 | Peers-Trevarton | |
| 4,632,121 A | 12/1986 | Johnson et al. | |
| 4,700,997 A | 10/1987 | Strand | |
| 4,702,256 A | 10/1987 | Robinson et al. | |
| 4,761,143 A | 8/1988 | Owens et al. | |
| 4,858,810 A | 8/1989 | Intlekofer et al. | |
| 4,860,742 A | 8/1989 | Park et al. | |
| 4,973,329 A | 11/1990 | Park et al. | |
| 5,159,861 A | 11/1992 | Anderson | |
| 5,178,159 A | 1/1993 | Christian | |
| 5,217,435 A | 6/1993 | Kring | |
| 5,325,746 A | 7/1994 | Anderson | |
| 5,325,868 A | 7/1994 | Kimmelstiel | |
| 5,334,045 A | 8/1994 | Cappa et al. | |
| 5,354,326 A | 10/1994 | Comben et al. | |
| 5,407,368 A | 4/1995 | Strand et al. | |
| 5,423,877 A | 6/1995 | Mackey | |
| 5,437,277 A | 8/1995 | Dumoulin et al. | |
| 5,454,739 A | 10/1995 | Strand | |
| 5,482,038 A | 1/1996 | Ruff | |
| 5,489,225 A | 2/1996 | Julian | |
| 5,501,675 A | 3/1996 | Erskine | |
| 5,538,444 A | 7/1996 | Strand et al. | |
| 5,560,358 A | 10/1996 | Arnold et al. | |
| 5,591,119 A | 1/1997 | Adair | |
| 5,624,281 A | 4/1997 | Christensson | |
| 5,685,855 A | 11/1997 | Erskine | |
| 5,752,915 A | 5/1998 | Neubauer et al. | |
| 5,766,042 A | 6/1998 | Ries et al. | |
| 5,769,786 A | 6/1998 | Wiegel | |
| 5,797,880 A | 8/1998 | Erskine | |
| 5,840,024 A | 11/1998 | Taniguchi et al. | |
| 5,968,082 A | 10/1999 | Heil | |
| 5,984,918 A | 11/1999 | Garito et al. | |
| 6,050,976 A | 4/2000 | Thorne et al. | |
| 6,090,052 A | 7/2000 | Akerfeldt et al. | |
| 6,102,044 A | 8/2000 | Naidyhorski | |
| 6,132,368 A | 10/2000 | Cooper | |
| 6,140,722 A * | 10/2000 | Ballard | H02K 15/0006 |
| | | | 310/71 |
| 6,162,101 A | 12/2000 | Fischer et al. | |
| 6,324,416 B1 | 11/2001 | Seibert | |
| 6,330,480 B1 | 12/2001 | Van der Linden et al. | |
| 6,350,160 B1 | 2/2002 | Feuersanger et al. | |
| 6,415,168 B1 | 7/2002 | Putz | |
| 6,428,336 B1 | 8/2002 | Akerfeldt | |
| 6,546,270 B1 | 4/2003 | Goldin et al. | |
| 6,620,136 B1 | 9/2003 | Pressly, Sr. et al. | |
| 6,663,570 B2 | 12/2003 | Mott et al. | |
| 6,673,078 B1 | 1/2004 | Muncie | |
| 6,714,809 B2 | 3/2004 | Lee et al. | |
| 6,780,065 B2 | 8/2004 | Schwarz | |
| 6,799,991 B2 | 10/2004 | Williams et al. | |
| 6,913,478 B2 | 7/2005 | Lamirey | |
| 7,130,699 B2 | 10/2006 | Huff et al. | |
| 7,144,378 B2 | 12/2006 | Arnott | |
| 7,255,609 B1 | 8/2007 | Epstein | |
| 7,274,956 B2 | 9/2007 | Mott et al. | |
| 7,402,083 B2 | 7/2008 | Kast et al. | |
| 7,452,360 B2 | 11/2008 | Trudeau et al. | |
| 7,553,193 B2 | 6/2009 | Kast et al. | |
| 7,585,118 B1 | 9/2009 | Lumpkin | |
| 7,633,023 B1 | 12/2009 | Cappa et al. | |
| 7,666,191 B2 | 2/2010 | Orban, III et al. | |
| 7,753,696 B2 | 7/2010 | Hoecke et al. | |
| 7,771,394 B2 | 8/2010 | Shue et al. | |
| 7,819,844 B2 | 10/2010 | Spenser et al. | |
| 7,972,282 B2 | 7/2011 | Clark et al. | |
| 8,105,338 B2 | 1/2012 | Anderson et al. | |
| 8,147,275 B1 | 4/2012 | Drake et al. | |
| 8,206,175 B2 | 6/2012 | Boyd et al. | |
| 8,267,873 B2 | 9/2012 | Yanuma | |
| 8,388,541 B2 | 3/2013 | Messerly et al. | |
| 8,480,427 B2 | 7/2013 | Marshalok | |
| 8,548,601 B2 | 10/2013 | Chinn et al. | |
| 8,597,042 B2 | 12/2013 | King | |
| 8,603,011 B2 | 12/2013 | Landowski | |
| 8,620,412 B2 | 12/2013 | Griffiths et al. | |
| 8,639,340 B2 | 1/2014 | Sommer et al. | |
| 8,666,510 B2 | 3/2014 | Chinn et al. | |
| 8,781,555 B2 | 7/2014 | Burnside et al. | |
| 8,849,382 B2 | 9/2014 | Cox et al. | |
| 8,869,887 B2 * | 10/2014 | Deere | E21B 47/00 |
| | | | 166/242.6 |
| 8,932,258 B2 | 1/2015 | Blanchard et al. | |
| 8,958,878 B2 | 2/2015 | Cejnar | |
| 9,059,548 B2 | 6/2015 | Stump et al. | |
| 9,095,680 B2 | 8/2015 | Steegers et al. | |
| 9,101,775 B2 | 8/2015 | Barker | |
| 9,107,594 B2 | 8/2015 | Selvitelli et al. | |
| 9,108,027 B2 | 8/2015 | Eubanks et al. | |
| 9,131,956 B2 | 9/2015 | Shaughnessy et al. | |
| 9,144,395 B2 | 9/2015 | Sela et al. | |
| 9,425,537 B2 | 8/2016 | Barker | |
| 9,456,766 B2 | 10/2016 | Cox et al. | |
| 9,492,097 B2 | 11/2016 | Wilkes et al. | |
| 9,521,961 B2 | 12/2016 | Silverstein et al. | |
| 9,526,440 B2 | 12/2016 | Burnside et al. | |
| 9,549,685 B2 | 1/2017 | Cox et al. | |
| 9,554,716 B2 | 1/2017 | Burnside et al. | |
| 9,636,031 B2 | 5/2017 | Cox | |
| 9,649,048 B2 | 5/2017 | Cox et al. | |
| 9,656,093 B2 | 5/2017 | Villarta et al. | |
| 9,662,506 B2 | 5/2017 | Govea | |
| 9,675,784 B2 | 6/2017 | Belson | |
| 9,681,823 B2 | 6/2017 | Messerly et al. | |
| 9,808,647 B2 * | 11/2017 | Rhodes | A61N 5/0624 |
| 9,872,971 B2 | 1/2018 | Blanchard | |
| 9,919,145 B2 | 3/2018 | Bondhus et al. | |
| 9,950,139 B2 | 4/2018 | Blanchard et al. | |
| 9,999,371 B2 | 6/2018 | Messerly et al. | |
| 10,105,121 B2 | 10/2018 | Burnside et al. | |
| 10,130,806 B2 | 11/2018 | Leven et al. | |
| 10,165,962 B2 | 1/2019 | Messerly et al. | |
| 10,201,713 B2 | 2/2019 | Leven | |
| 10,231,753 B2 | 3/2019 | Burnside et al. | |
| 10,238,418 B2 | 3/2019 | Cox et al. | |
| 10,238,880 B2 | 3/2019 | Thom et al. | |
| 10,307,602 B2 | 6/2019 | Leven | |
| 10,322,253 B2 * | 6/2019 | Einav | A61M 16/0459 |
| 10,342,575 B2 | 7/2019 | Cox et al. | |
| 10,449,330 B2 | 10/2019 | Newman et al. | |

(56) References Cited

U.S. PATENT DOCUMENTS

| | | | |
|---|---|---|---|
| 10,524,691 B2 | 1/2020 | Newman et al. | |
| 10,602,958 B2 | 3/2020 | Silverstein et al. | |
| 10,751,509 B2 | 8/2020 | Misener | |
| 10,772,696 B2 | 9/2020 | Thompson et al. | |
| D921,884 S | 6/2021 | Tran et al. | |
| 2002/0197905 A1 | 12/2002 | Kaufmann et al. | |
| 2003/0199827 A1 | 10/2003 | Thorne | |
| 2003/0216723 A1 | 11/2003 | Shinmura et al. | |
| 2004/0039372 A1 | 2/2004 | Carmody | |
| 2005/0177199 A1 | 8/2005 | Hansen et al. | |
| 2005/0283216 A1 | 12/2005 | Pyles | |
| 2006/0025677 A1 | 2/2006 | Verard et al. | |
| 2006/0030864 A1* | 2/2006 | Kennedy, II | A61F 2/954 606/108 |
| 2006/0173407 A1 | 8/2006 | Shaughnessy et al. | |
| 2007/0062544 A1 | 3/2007 | Rauk Bergstrom et al. | |
| 2007/0118079 A1 | 5/2007 | Moberg et al. | |
| 2007/0160327 A1 | 7/2007 | Lewallen et al. | |
| 2007/0161969 A1 | 7/2007 | Andersen | |
| 2007/0293719 A1 | 12/2007 | Scopton et al. | |
| 2008/0009720 A1 | 1/2008 | Schefelker et al. | |
| 2008/0046062 A1 | 2/2008 | Camps et al. | |
| 2008/0236598 A1 | 10/2008 | Gobel | |
| 2008/0287876 A1 | 11/2008 | Shue et al. | |
| 2008/0304793 A1 | 12/2008 | Benaron et al. | |
| 2009/0156926 A1* | 6/2009 | Messerly | A61B 5/283 600/409 |
| 2009/0234328 A1 | 9/2009 | Cox et al. | |
| 2010/0036227 A1* | 2/2010 | Cox | A61B 8/0833 600/509 |
| 2010/0139669 A1 | 6/2010 | Piferi et al. | |
| 2010/0204569 A1* | 8/2010 | Burnside | A61B 8/0833 604/272 |
| 2011/0160824 A1 | 6/2011 | Ware et al. | |
| 2011/0166528 A1 | 7/2011 | Millerd et al. | |
| 2011/0250775 A1 | 10/2011 | Bies et al. | |
| 2011/0257503 A1 | 10/2011 | Mehdizadeh et al. | |
| 2012/0071752 A1* | 3/2012 | Sewell | A61B 34/71 345/650 |
| 2012/0253320 A1 | 10/2012 | Steegers et al. | |
| 2013/0023729 A1* | 1/2013 | Vazales | A61B 90/70 600/109 |
| 2013/0095689 A1* | 4/2013 | Hayman | H01R 13/622 439/359 |
| 2013/0104884 A1* | 5/2013 | Vazales | A61M 16/0463 128/202.16 |
| 2013/0109980 A1 | 5/2013 | Teo | |
| 2013/0211225 A1 | 8/2013 | Zhang | |
| 2013/0247921 A1 | 9/2013 | Dye et al. | |
| 2013/0289417 A1 | 10/2013 | Grunwald et al. | |
| 2013/0308137 A1 | 11/2013 | Manzke et al. | |
| 2013/0331688 A1 | 12/2013 | Heigl et al. | |
| 2013/0337674 A1 | 12/2013 | Stump et al. | |
| 2014/0150782 A1* | 6/2014 | Vazales | A61M 25/1018 128/202.16 |
| 2015/0012072 A1 | 1/2015 | Johnson et al. | |
| 2015/0031987 A1 | 1/2015 | Pameijer et al. | |
| 2015/0105654 A1 | 4/2015 | Meyer | |
| 2015/0148615 A1 | 5/2015 | Brennan et al. | |
| 2015/0164583 A1 | 6/2015 | Zarins et al. | |
| 2015/0190615 A1 | 7/2015 | Shaltis | |
| 2015/0223897 A1 | 8/2015 | Kostrzewski et al. | |
| 2015/0305816 A1 | 10/2015 | Hadzic | |
| 2016/0018602 A1 | 1/2016 | Govari et al. | |
| 2017/0231700 A1 | 8/2017 | Cox et al. | |
| 2017/0261699 A1 | 9/2017 | Compton et al. | |
| 2017/0333136 A1 | 11/2017 | Hladio et al. | |
| 2018/0071509 A1 | 3/2018 | Tran et al. | |
| 2018/0110951 A2 | 4/2018 | Beard | |
| 2018/0140170 A1 | 5/2018 | Van Putten et al. | |
| 2018/0289927 A1 | 10/2018 | Messerly | |
| 2019/0069877 A1 | 3/2019 | Burnside et al. | |
| 2019/0231172 A1 | 8/2019 | Barron et al. | |
| 2019/0237902 A1 | 8/2019 | Thompson et al. | |
| 2019/0350621 A1 | 11/2019 | Zitnick et al. | |
| 2019/0350663 A1* | 11/2019 | Thompson | A61B 46/23 |
| 2020/0345441 A1 | 11/2020 | Thompson et al. | |
| 2021/0030504 A1 | 2/2021 | Thompson et al. | |
| 2021/0038322 A1 | 2/2021 | Thompson et al. | |
| 2022/0110707 A1 | 4/2022 | Sowards et al. | |
| 2022/0110708 A1 | 4/2022 | Misener et al. | |
| 2022/0128770 A1 | 4/2022 | Sowards et al. | |

FOREIGN PATENT DOCUMENTS

| | | |
|---|---|---|
| EP | 3673801 A1 | 7/2020 |
| WO | 9413201 A1 | 6/1994 |
| WO | 9619017 A1 | 6/1996 |
| WO | 9822180 A1 | 5/1998 |
| WO | 2004101068 A1 | 11/2004 |
| WO | 2005016451 A1 | 2/2005 |
| WO | 2005044332 A2 | 5/2005 |
| WO | 2005072807 A1 | 8/2005 |
| WO | 2005077453 A2 | 8/2005 |
| WO | 2007058816 A2 | 5/2007 |
| WO | 2007109285 A2 | 9/2007 |
| WO | 2007149618 A2 | 12/2007 |
| WO | 2009050599 A2 | 4/2009 |
| WO | 2010123701 A1 | 10/2010 |
| WO | 2011033107 A1 | 3/2011 |
| WO | 2011082160 A2 | 7/2011 |
| WO | 2012102745 A2 | 8/2012 |
| WO | 2015075002 A1 | 5/2015 |
| WO | 2016/146993 A1 | 9/2016 |
| WO | 2019/148201 A1 | 8/2019 |
| WO | 2019/165011 A1 | 8/2019 |
| WO | 2019/221926 A1 | 11/2019 |
| WO | 2021021408 A1 | 2/2021 |
| WO | 2021026502 A1 | 2/2021 |
| WO | 2022/081583 A1 | 4/2022 |
| WO | 2022081591 A1 | 4/2022 |
| WO | 2022/093991 A1 | 5/2022 |

OTHER PUBLICATIONS

PCT/US2019/015710 filed Jan. 29, 2019 International Preliminary Report on Patentability dated Apr. 29, 2019.
PCT/US2019/015710 filed Jan. 29, 2019 International Search Report and Written Opinion dated Apr. 29, 2019.
PCT/US2019/018851 filed Feb. 20, 2019 Internation Search Report and Written Opinion dated May 7, 2019.
PCT/US2019/018851 filed Feb. 20, 2019 International Preliminary Report on Patentability dated May 7, 2019.
PCT/US2020/41267 filed Jul. 8, 2020 Internation Search Report and Written Opinion dated Oct. 1, 2020.
PCT/US2020/45498 filed Aug. 7, 2020 International Search Report and Written Opinion dated Oct. 4, 2020.
PCT/US2021/054593 filed Oct. 12, 2021 International Search Report and Written Opinion dated Jan. 24, 2022.
PCT/US2021/054607 filed Oct. 12, 2021 International Search Report and Written Opinion dated Jan. 21, 2022.
PCT/US2021/056896 filed Oct. 27, 2021 International Search Report and Written Opinion dated Mar. 22, 2022.
U.S. Appl. No. 12/426,175, filed Apr. 17, 2009 Advisory Action dated Nov. 26, 2013.
U.S. Appl. No. 12/426,175, filed Apr. 17, 2009 Decision on Appeal dated Nov. 7, 2016.
U.S. Appl. No. 12/426,175, filed Apr. 17, 2009 Examiner's Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/715,556, filed Mar. 2, 2010 Final Office Action dated Oct. 2, 2013.

(56) References Cited

OTHER PUBLICATIONS

U.S. Appl. No. 12/715,556, filed Mar. 2, 2010 Non-Final Office Action dated Sep. 13, 2012.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 16/261,368, filed Jan. 29, 2019 Advisory Action dated Jul. 21, 2020.
U.S. Appl. No. 16/261,368, filed Jan. 29, 2019 Non-Final Office Action dated Jan. 23, 2020.
U.S. Appl. No. 16/261,368, filed Jan. 29, 2019 Notice of Allowance dated Jan. 15, 2021.
U.S. Appl. No. 16/281,079, filed Feb. 20, 2019 Examiner's Answer dated Feb. 25, 2022.
U.S. Appl. No. 16/281,079, filed Feb. 20, 2019 Final Office Action dated Aug. 25, 2020.
U.S. Appl. No. 16/281,079, filed Feb. 20, 2019 Non-Final Office Action dated Apr. 1, 2020.
U.S. Appl. No. 16/281,079, filed Feb. 20, 2019 Non-Final Office Action dated Apr. 20, 2021.
U.S. Appl. No. 16/402,074, filed May 2, 2019 Non-Final Office Action dated Apr. 16, 2020.
U.S. Appl. No. 16/932,425, filed Jul. 17, 2020 Non-Final Office Action dated Jun. 18, 2021.
U.S. Appl. No. 16/932,425, filed Jul. 17, 2020 Notice of Allowance dated Jan. 10, 2022.
Design U.S. Appl. No. 29/658,136 Specification and Drawings filed Jul. 27, 2018.

* cited by examiner

CONNECTION SYSTEMS AND METHODS THEREOF FOR ESTABLISHING AN ELECTRICAL CONNECTION THROUGH A DRAPE

PRIORITY

This application is a continuation of U.S. patent application Ser. No. 16/932,425, filed Jul. 17, 2020, now U.S. Pat. No. 11,304,772, which is a continuation of U.S. patent application Ser. No. 16/402,074, filed May 2, 2019, now U.S. Pat. No. 10,772,696, which claims the benefit of priority to U.S. Provisional Application No. 62/673,726, filed May 18, 2018, titled "Vertical Thru-Drape Connection System For Medical Device Placement System," each of which is incorporated by reference in its entirety into this application.

BACKGROUND

In a typical surgical procedure, a sterile drape is placed over a patient to establish a sterile field, within which the surgical procedure is performed. For example, in a typical catheter-placement procedure, a sterile drape is placed over a patient to establish a sterile field for placement of the catheter. However, there is often a need to breach the sterile barrier in order to make electrical connections between components of various systems without compromising the sterility of the sterile field.

Disclosed herein is a connection system for establishing an electrical connection through a drape and methods thereof that address at least the foregoing need.

SUMMARY

Disclosed herein is a connection system for establishing one or more electrical connections through a drape. The connection system includes, in some embodiments, a first connector and a second connector configured to connect to each other. The first connector includes a first-connector housing, an electrical lead extending from the first-connector housing, and at least a first piercing element within the first-connector housing configured to pierce the drape. The first piercing element is orthogonally connected to the electrical lead. The second connector includes a second-connector housing and at least a first receptacle within the second-connector housing. The first receptacle is configured to form at least a first electrical connection of the one or more electrical connections with the first piercing element when the first connector is disposed over the second connector with the drape therebetween.

In some embodiments, the first-connector housing includes an integrated clip configured to clip the first connector on the second connector with the drape between the first connector and the second connector.

In some embodiments, the integrated clip includes a pair of opposing tabs. Each tab of the pair of tabs extends from a medial portion of a major side of the first-connector housing to a perimeter about an opening of the first-connector housing. The perimeter about the opening of the first-connector housing is shared by all sides of the first-connector housing.

In some embodiments, the second-connector housing includes a pair of opposing protrusions. Each protrusion of the pair of protrusions protrudes from a medial portion of a major side of the second-connector housing. Each tab of the pair of tabs of the first-connector housing includes a through hole configured to accept a protrusion of the pair of protrusions.

In some embodiments, each tab of the pair of tabs of the first-connector housing is flared away from the other tab of the pair of tabs. Each protrusion of the pair of protrusions of the second-connector housing is beveled or chamfered. A combination of the flared tabs and the beveled or chamfered protrusions facilitate disposal of the first connector over the second connector.

In some embodiments, each tab of the pair of tabs of the first-connector housing is flexibly attached to the first-connector housing to facilitate removal of the first connector from the second connector by deflecting each tab away from the other tab.

In some embodiments, minor sides of each housing of the first-connector housing and the second-connector housing are dissimilar. Each minor side of the minor sides of the first-connector housing have a matching minor side of the minor sides of the second-connector housing. This enforces a single orientation of the first connector when disposing the first connector over the second connector.

In some embodiments, the first piercing element is a jack plug having a needle-like tip electrical contact, one or more ring electrical contacts, and a sleeve electrical contact. The first receptacle is a jack having complementary electrical contacts.

In some embodiments, the connection system further includes a second piercing element and a third piercing element within the first-connector housing and a second receptacle and a third receptacle within the second-connector housing. The second piercing element and the third piercing element are orthogonally connected to the electrical lead. Each piercing element of the first, second, and third piercing elements are configured to pierce the drape in a different location than the other piercing elements. The second receptacle and the third receptacle are configured to form at least a second electrical connection and a third electrical connection of the one or more electrical connections respectively with the second piercing element and the third piercing element when the first connector is disposed over the second connector with the drape therebetween.

In some embodiments, the first-connector housing includes a pair of opposing finger pads configured for pushing the first connector onto the second connector or pulling the first connector off of the second connector. Each finger pad of the pair of finger pads includes a depression between the medial portion of the major side of the first-connector housing including the finger pad and a closed end of the first-connector housing.

Also disclosed herein is a connection system for establishing a plurality of electrical connections through a drape. The connection system includes, in some embodiments, a tether connector and a fin connector configured to connect to each other. The tether connector is coupled to a stylet configured to be removably disposed in a catheter. The tether connector includes a tether-connector housing, an electrical lead extending from the tether-connector housing, and a plurality of piercing elements within the tether-connector housing. The tether-connector housing includes an integrated clip having an opposing pair of tabs. Each tab of the pair of tabs includes a through hole. The plurality of piercing elements within the tether-connector housing are orthogonally connected to the electrical lead extending from the tether-connector housing. Each piercing element of the plurality of piercing elements is configured to pierce a sterile side of the drape in a different location than the other piercing elements. The fin connector is part of a tip-location sensor configured to sense a location of a tip of the catheter when the stylet is disposed in the catheter. The fin connector includes a fin-connector housing and a plurality of receptacles within the fin-connector housing. The fin-connector housing includes a pair of opposing protrusions. Each protrusion of the pair of protrusions is configured to insert into a corresponding through hole of the pair of tabs of the tether connector housing for clipping the tether connector to the fin connector. The plurality of receptacles within the fin-connector housing are orthogonal to a body of the tip-location sensor. The plurality of receptacles are configured to form the plurality of electrical connections with the plurality of piercing elements when the tether connector is disposed over the fin connector with the drape therebetween.

In some embodiments, each tab of the pair of tabs of the tether-connector housing extends from a medial portion of a major side of the tether-connector housing to a perimeter about an opening of the tether-connector housing. The perimeter about the opening of the tether-connector housing is shared by all sides of the tether-connector housing. Each protrusion of the pair of protrusions of the fin-connector housing protrudes from a medial portion of a major side of the fin-connector housing.

In some embodiments, each tab of the pair of tabs of the tether-connector housing is flared away from the other tab of the pair of tabs. Each protrusion of the pair of protrusions of the fin connector is beveled or chamfered. A combination of the flared tabs and the beveled or chamfered protrusions facilitate disposal of the tether connector over the fin connector.

In some embodiments, each tab of the pair of tabs of the tether-connector housing is flexibly attached to the tether-connector housing to facilitate removal of the tether connector from the fin connector by deflecting each tab away from the other tab.

In some embodiments, minor sides of each housing of the tether-connector housing and the fin-connector housing are dissimilar. Each minor side of the minor sides of the tether-connector housing having a matching minor side of the minor sides of the fin-connector housing. This enforces a single orientation of the tether connector when disposing the tether connector over the fin connector.

In some embodiments, the tether-connector housing includes a pair of opposing finger pads configured for pushing the tether connector onto the fin connector or pulling the tether connector off of the fin connector. Each finger pad of the pair of finger pads includes a depression between the medial portion of the major side of the tether-connector housing including the finger pad and a closed end of the tether-connector housing.

Also disclosed herein is a method for establishing one or more electrical connections through a drape with a connection system. The method includes, in some embodiments, placing the drape over a second connector of a connection system, the second connector including a second-connector housing having dissimilar minor sides; aligning a first connector of the connection system with the second connector, the first connector including a first-connector housing having dissimilar minor sides; disposing the first connector over the second connector with the drape between the first connector and the second connector, the drape self-tightening over the second connector during the disposing of the first connector over the second connector; piercing a sterile side of the drape with at least a first piercing element within the first-connector housing orthogonally connected to an electrical lead extending from the first-connector housing; inserting the first piercing element into at least a first receptacle within the second-connector housing; and forming the one or more electrical connections between the first piercing element of the first connector and the first receptacle of the second connector. Aligning the first connector of the connection system with the second connector includes matching each minor side of the minor sides of the first-connector housing with a matching minor side of the minor sides of the second-connector housing, thereby enforcing a single orientation of the first connector to the second connector.

In some embodiments, disposing the first connector over the second connector includes inserting each protrusion of a pair of opposing protrusions protruding from a medial portion of a major side of the second-connector housing into a corresponding through hole of a tab of a pair of opposing tabs extending from a medial portion of a major side of the first-connector housing.

In some embodiments, piercing the sterile side of the drape with the first piercing element includes simultaneously piercing the sterile side of the drape in two other locations with a second and a third piercing element within the first-connector housing orthogonally connected to the electrical lead extending from the first-connector housing.

In some embodiments, the method further includes disposing a stylet in a catheter, the first connector being a tether connector coupled to the stylet; and sensing a location of a tip of the catheter in a patient, the second connector being a fin connector of a tip-location sensor on a chest of the patient under the drape. Disposing the first connector over the second connector includes disposing the tether connector over the fin connector with a downward motion substantially orthogonal to the tip-location sensor.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

In a typical surgical procedure, a sterile drape is placed over a patient to establish a sterile field, within which the surgical procedure is performed. For example, in a typical catheter-placement procedure, a sterile drape is placed over a patient to establish a sterile field for placement of the catheter. However, there is often a need to breach the sterile barrier in order to make electrical connections between components of various systems without compromising the sterility of the sterile field.

Disclosed herein is a connection system for establishing an electrical connection through a drape and methods thereof that address at least the foregoing need.

For example, a connection system includes, in some embodiments, a first connector and a second connector configured to connect to each other. The first connector includes a first-connector housing, an electrical lead extending from the first-connector housing, and at least a first piercing element within the first-connector housing configured to pierce the drape. The first piercing element is orthogonally connected to the electrical lead. The second connector includes a second-connector housing and at least a first receptacle within the second-connector housing. The first receptacle is configured to form at least a first electrical connection of the one or more electrical connections with the first piercing element when the first connector is disposed over the second connector with the drape therebetween. An example method for establishing one or more electrical connections through the drape with the foregoing connection system is set forth below.

An example catheter-placement system incorporating the connection system will be at least initially described to provide context for the connection system. It should be understood the connection system is not limited to the example catheter-placement system. Indeed, the connection system can be incorporated into any system of various systems having a need to breach a sterile barrier between components of the system in order to make electrical connections therebetween without compromising the sterility of the sterile field.

Figure 1:
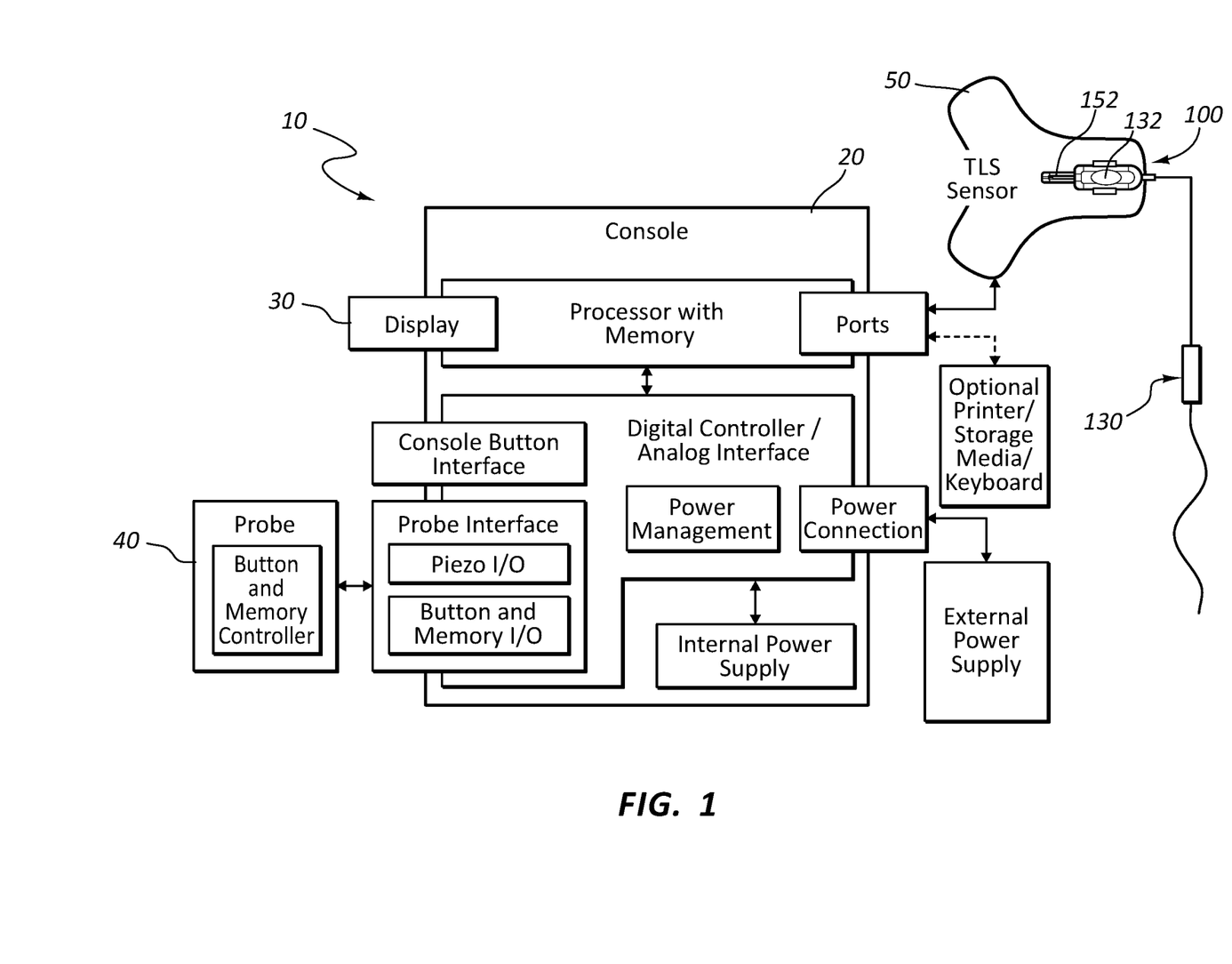
FIG. 1 illustrates a block diagram of a catheter-placement system for placing a catheter in a body of a patient in accordance with some embodiments.
Figure 2:
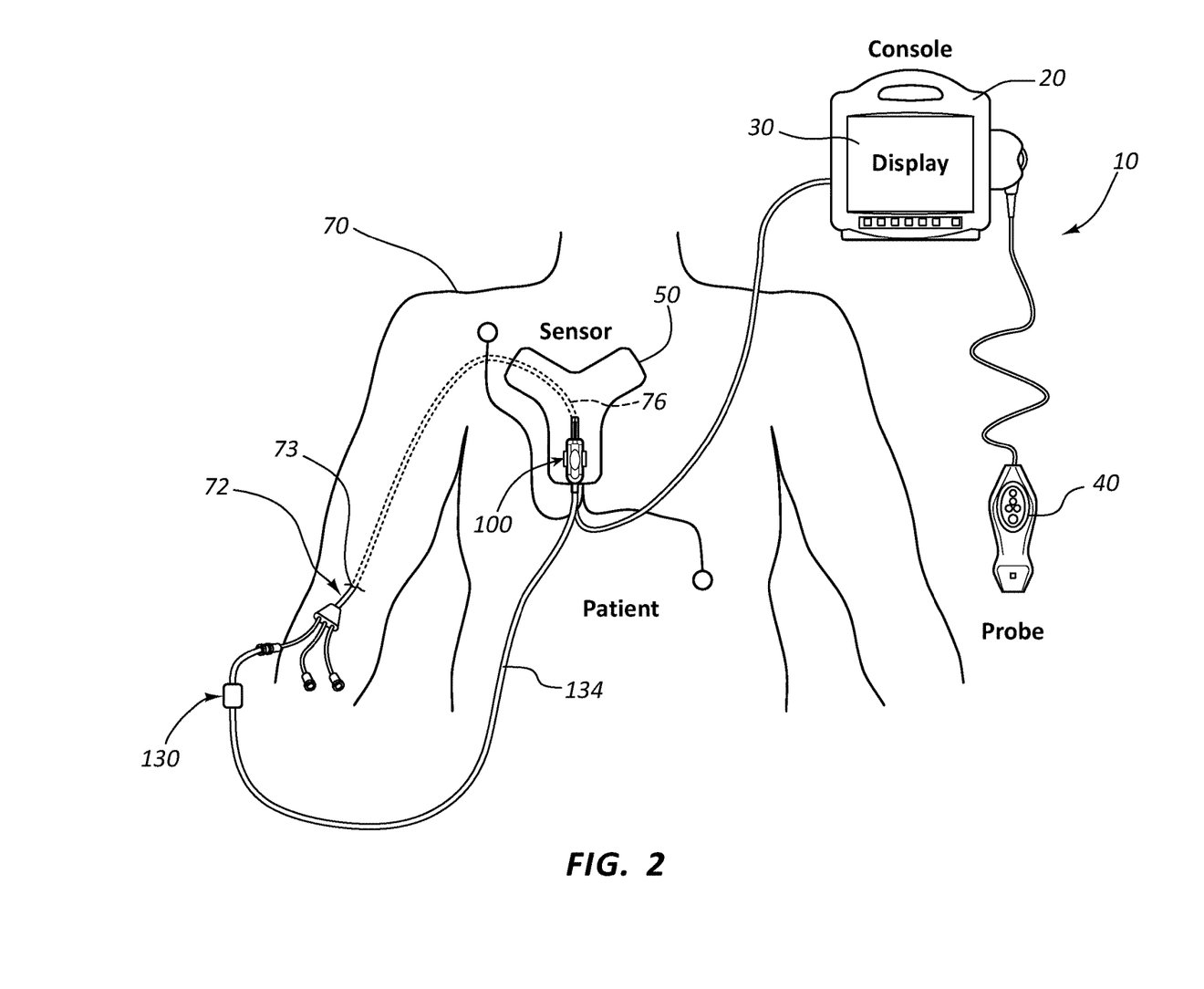
FIG. 2 illustrates the catheter-placement system and the patient in accordance with some embodiments.

FIG. 1 illustrates a block diagram of a catheter-placement system 10 for placing a catheter 72 in a body of a patient 70 in accordance with some embodiments. FIG. 2 illustrates the catheter-placement system 10 and the patient 70 in accordance with some embodiments. The catheter-placement system 10 is configured for assisting a clinician in placing the catheter 72 in a vasculature of the patient 70. As shown, the catheter-placement system 10 includes a console 20 including a display 30, an ultrasound probe 40, and a tip-location sensor 50 configured for placement on the patient's chest or some other portion of the patient's body.

Figure 3:
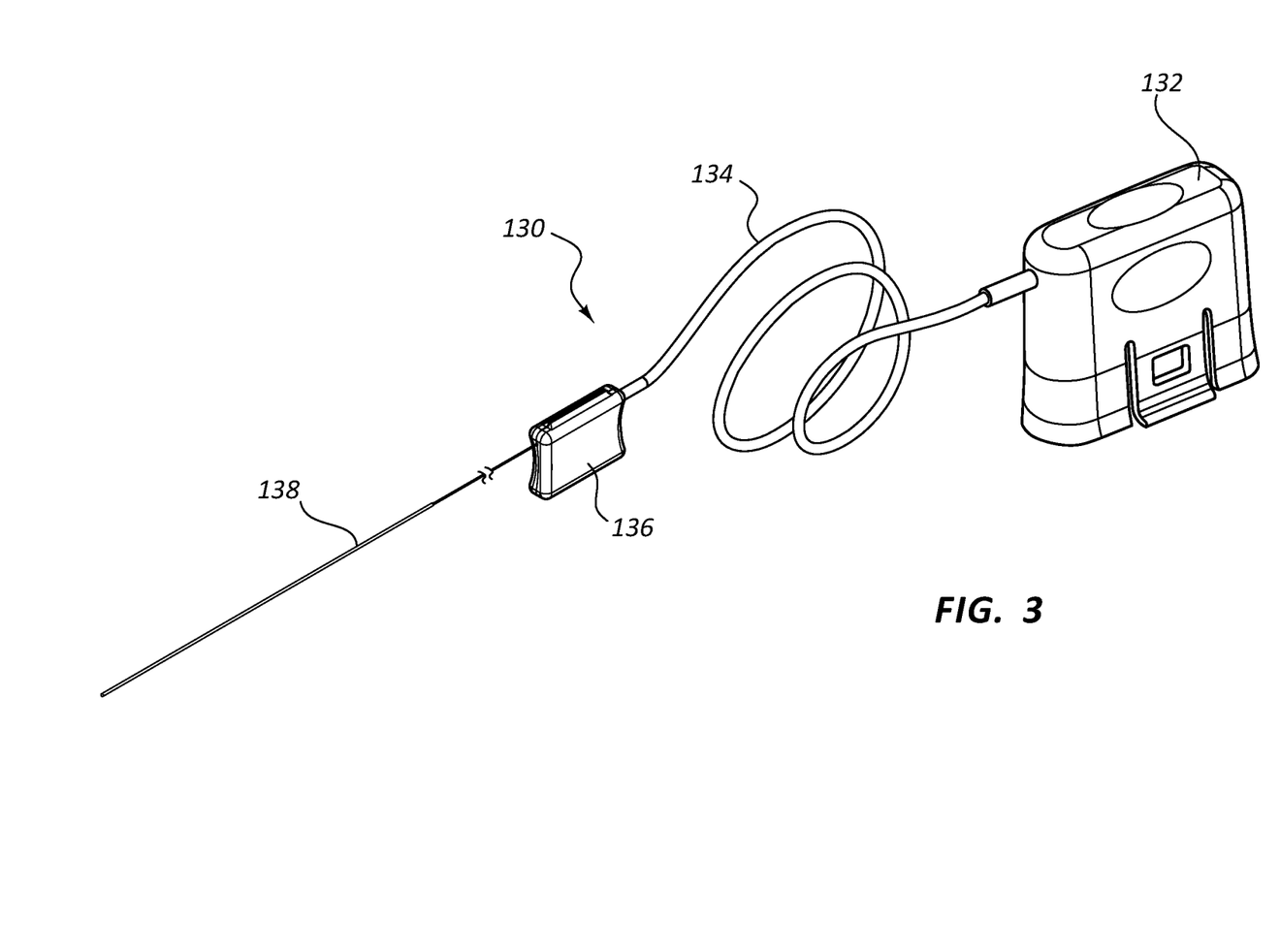
FIG. 3 illustrates a stylet including a tether connector of the catheter-placement system in accordance with some embodiments.

FIG. 3 illustrates a stylet 130 including a tether connector 132 of the catheter-placement system 10 in accordance with some embodiments. The stylet 130 is employed with the catheter 72 during insertion of the catheter 72 into the vasculature of the patient 70. The stylet 130 includes a core wire 138 configured to be removably disposed in a lumen of the catheter 72 during a catheter-placement procedure, thereby enabling a distal tip 76 of the catheter 72 to be tracked by the catheter-placement system 10 using one or more of modalities for guiding the catheter 72 to a desired location within the patient's vasculature after insertion of the catheter 72 into a percutaneous insertion site 73 of the patient 70. The one or more modalities include, but are not limited to ultrasound-based imaging of subcutaneous tissue of the patient in preparation for insertion of the catheter 72; magnet-based tracking for determining orientation, advancement direction, and general internal location of the distal tip 76 of the catheter 72; or ECG-based confirmation for confirming the distal tip 76 of the catheter 72 is positioned at a desired location for which ECG lead connector 151 is provided. (See FIG. 4 for ECG lead connector 151.) The stylet 130 further includes a tether 134 proximally extending from a handle 136, the tether 134 terminating at a proximal end thereof with the tether connector 132. The tether connector 132 is configured to mechanically couple and electrically connect with a fin connector 152 of the tip-location sensor 50 as shown in at least FIGS. 1-4 in accordance with some embodiments of a connection system 100.

Additional details for the catheter-placement system 10 shown in FIGS. 1-3 can be found in U.S. Pat. No. 9,649,048, which is incorporated by reference in its entirety into this application.

Figure 4:
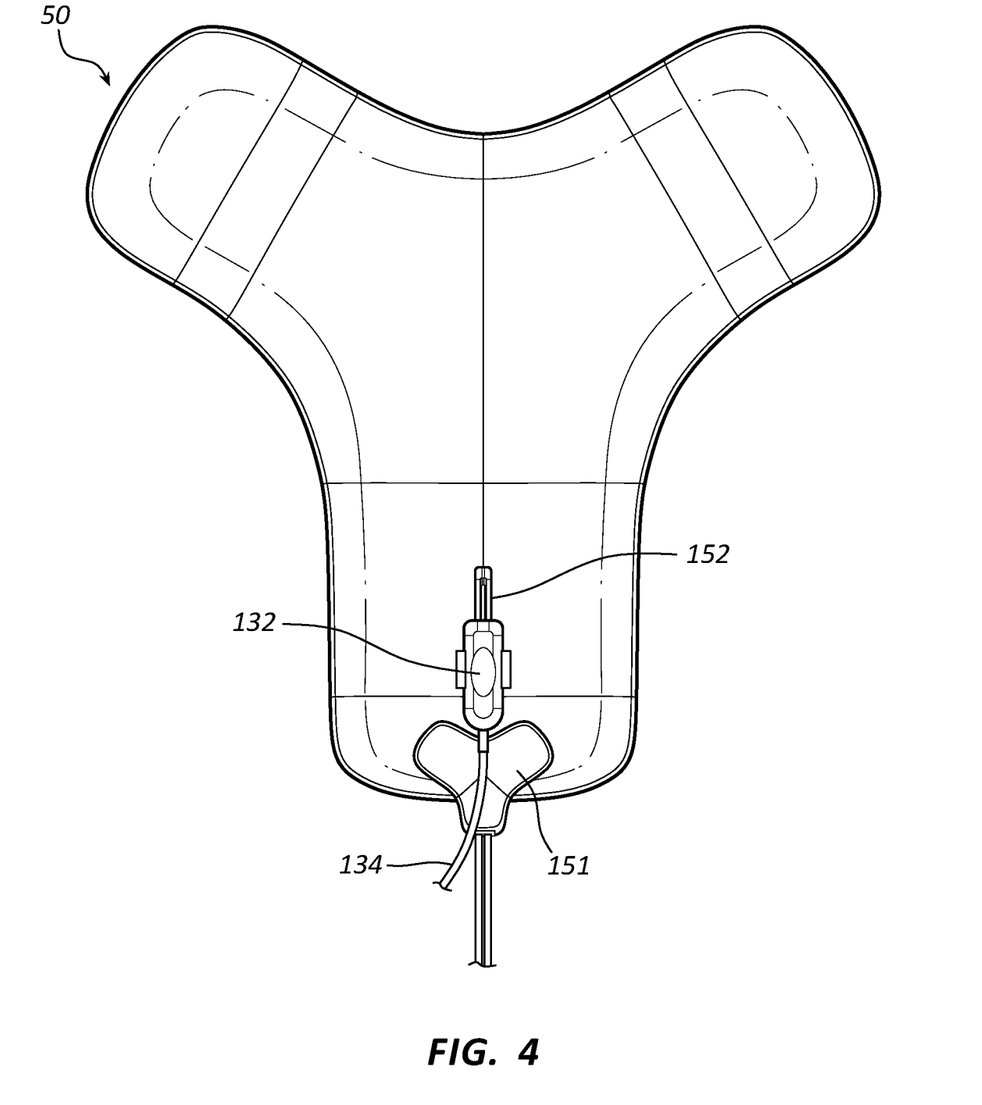
FIG. 4 illustrates a tip-location sensor including a fin connector of the catheter-placement system in accordance with some embodiments.
Figure 5:
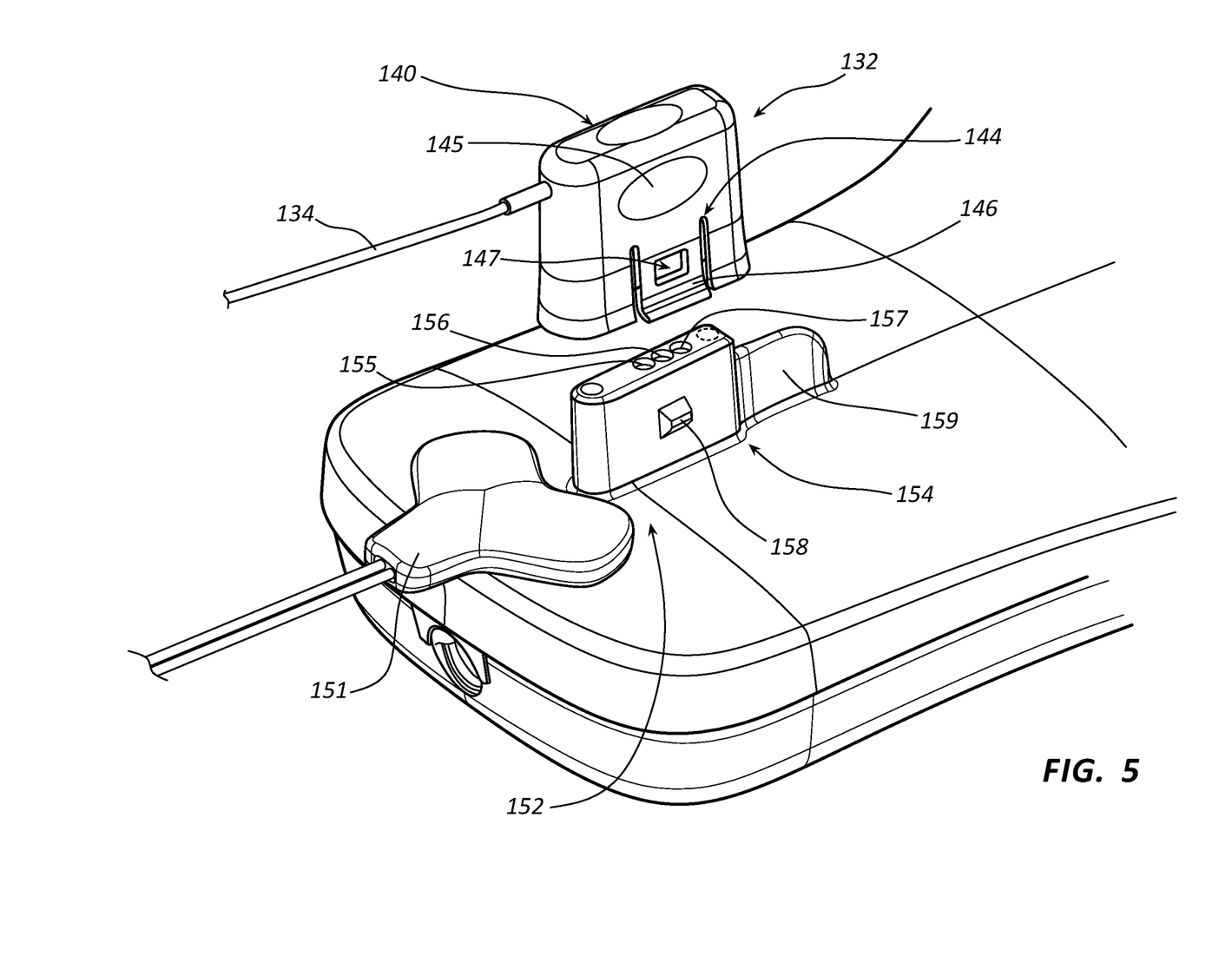
FIG. 5 illustrates a perspective view of a first connector and a second connector of a connection system in accordance with some embodiments.

FIG. 4 illustrates the tip-location sensor 50 and the fin connector 152 of the catheter-placement system 10 in accordance with some embodiments. As shown, the fin connector 152 is disposed on the tip-location sensor 50 of the catheter-placement system 10. Again, the tether connector 132 is configured to mechanically couple and electrically connect with the fin connector 152, which enables the catheter-placement system 10 to track the distal tip 76 of the catheter 72. A drape including a sterile drape is configured to provide a sterile field about the patient 70. The drape can be interposed between the tip-location sensor 50 (e.g., under the sterile drape in a non-sterile field) and the stylet 130 (e.g., over the sterile drape in the sterile field). As set forth in more detail below, the tether connector 132 includes at least a first piercing element 142 within a body of the tether connector 132, wherein the first piercing element 142 is configured to pierce the drape and insert into at least a first receptacle 156 of the fin connector 152 to electrically connect the tether connector 132 and the fin connector 152. As best shown in FIG. 5, at least the first receptacle 156 of one or more receptacles in the fin connector 152 is orthogonal to a body of the tip-location sensor 50.

While not shown in FIG. 4, the catheter-placement system 10, or the connection system 100 thereof, can include one or more light-emitting diodes ("LEDs") configured to change from a first state to a second state to indicate success in forming one or more electrical connections between the tether connector 132 and the fin connector 152. The one or more LEDs can include an LED on the tip-location sensor 50, an LED on the tether connector 132, or both of the foregoing LEDs. Upon success in forming the one or more electrical connections between the tether connector 132 and the fin connector 152, each LED of the one or more LEDs can change from a first state of being off to a second state of being on, a first state of being one color (e.g., red) to a second state of being another color (e.g., green), a first state of blinking light to a second state of a solid light, or various combinations thereof. Each LED of the one or more LEDs is configured to change from the first state to the second state upon completion of a dedicated LED circuit for the change of state upon forming the one or more electrical connections. The LED on the tip-location sensor 50 is configured to be bright enough to see through a drape, thus enabling a clinician to see a change from the first state to the second state upon forming one or more electrical connections between the tether connector 132 and the fin connector 152 even when the drape is in place.

In view of the foregoing catheter-placement system 10, the connection system 100 includes a first connector such as the tether connector 132 having the tether 134 and a second connector such as the fin connector 152 configured for mechanically coupling and establishing one or more electrical connections through a sterile drape without compromising the sterile field set up by the sterile drape. Having described the connection system 100 in the context of the catheter-placement system 10, additional details for the first connector and the second connector of the connection system 100 will now be described with the understanding the connection system 100 is not limited to the foregoing catheter-placement system 10. For convenience, the first connector and the second connector of the connection system 100 will now respectively assume the reference numerals 132 and 152. Likewise, an electrical lead of the first connector will now assume the reference numeral 134.

Figure 6:
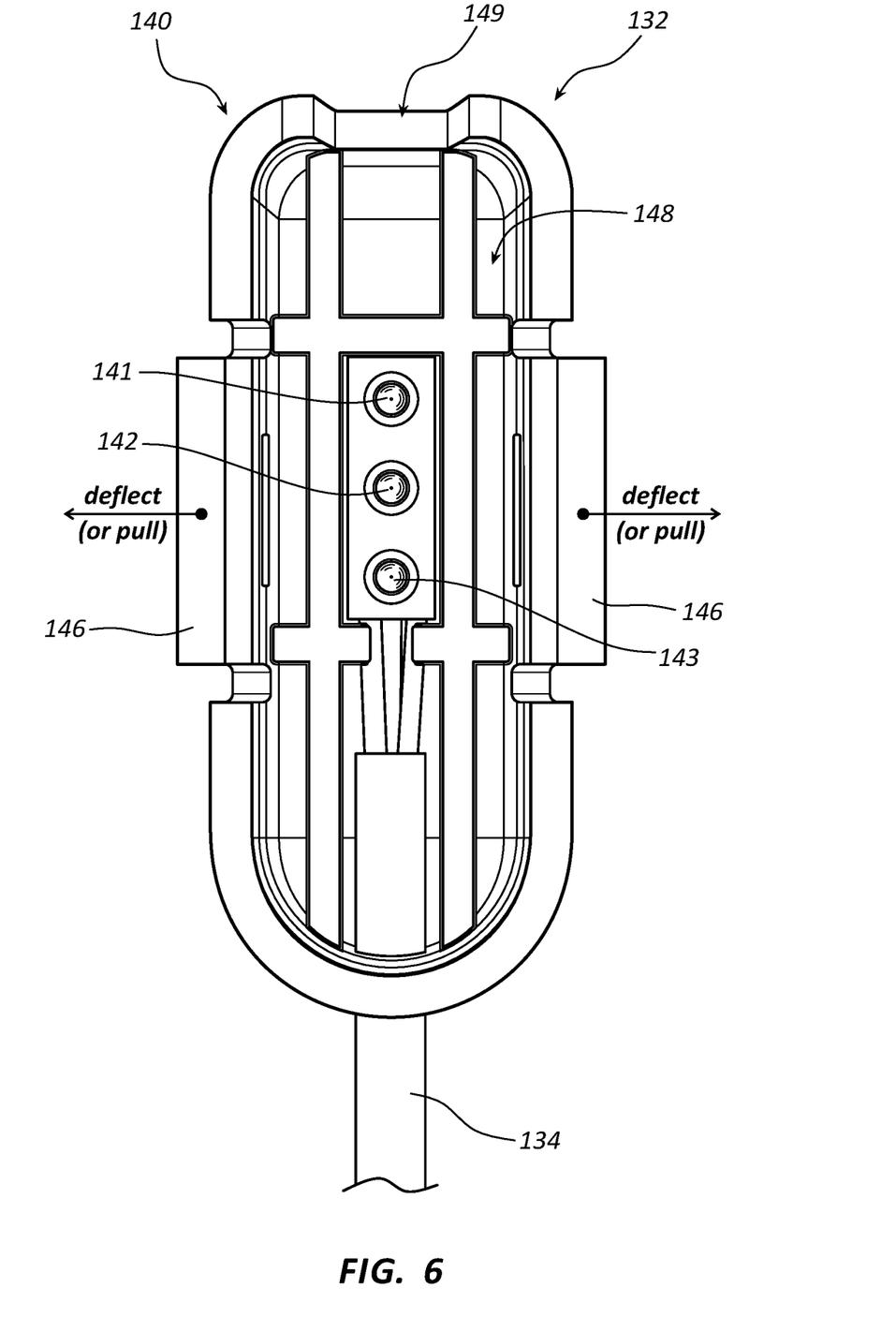
FIG. 6 illustrates a view within a housing of the first connector in accordance with some embodiments.

FIG. 5 illustrates a perspective view of the first connector 132 and the second connector 152 of the connection system 100 in accordance with some embodiments. FIG. 6 illustrates a view within a housing 140 of the first connector 132 in accordance with some embodiments.

Again, the connection system 100 includes the first connector 132 and the second connector 152, which are configured for mechanically coupling and establishing one or more electrical connections through a sterile drape without compromising the sterile field set up by the sterile drape. The first connector 132 includes the first-connector housing 140, the electrical lead 134 extending from the first-connector housing 140, and at least a first piercing element 142 having one or more electrical contacts within the first-connector housing 140 configured to pierce the sterile drape. The second connector 152 includes a second-connector housing 154 and at least a first receptacle 156 having one or more electrical contacts within the second-connector housing 154. Each housing of the first-connector housing 140 and the second-connector housing 154 is molded from a medically acceptable polymer such as a thermoplastic.

Beginning with the configuration of the first connector 132 and the second connector 152 of the connection system 100 for mechanically coupling the first connector 132 and the second connector 152, the first-connector housing 140 includes an integrated clip 144 configured to clip the first connector 132 on the second connector 152 with the drape between the first connector 132 and the second connector 152. The integrated clip 144 of the first-connector housing 140 includes a pair of opposing tabs 146 with a corresponding pair of through holes 147, of which through holes 147 only one through hole is shown in FIG. 5. Each tab of the pair of tabs 146 extends from a medial portion of a major side, or long side, of the first-connector housing 140 to a perimeter about a primary opening 148 (see FIG. 6) of the first-connector housing 140. The perimeter about the primary opening 148 of the first-connector housing 140 is shared by all sides of the first-connector housing 140. Because the first-connector housing 140 is molded of a medically acceptable polymer and each tab of the pair of tabs 146 extends from a medial portion of a major side of the first-connector housing 140, each tab of the pair of tabs 146 is flexibly attached to the first-connector housing 140. Each tab of the pair of tabs 146 of the first-connector housing 140 is also flared away from the other tab of the pair of tabs 146 as best shown in FIG. 6.

As a complement to the integrated clip 144 of the first-connector housing 140, the second-connector housing 154 includes a pair of opposing protrusions 158, of which pair of protrusions 158 only one protrusion is shown in FIG. 5. Each protrusion of the pair of protrusions 158 protrudes from a medial portion of a major side, or long side, of the second-connector housing 154. The protrusion in each major side of the second-connector housing 154 is configured to insert in a respective through hole of the pair of tabs 146. In other words, the through hole in each tab of the pair of tabs 146 of the first-connector housing 140 is configured to accept a respective protrusion of the pair of protrusions 158. Each protrusion of the pair of protrusions 158 of the second-connector housing 154 is beveled or chamfered as shown in FIG. 5.

A combination of the flared, flexibly attached pair of tabs 146 of first-connector housing 140 and the beveled or chamfered pair of protrusions 158 of the second-connector housing 154 facilitates disposal of the first connector 132 over the second connector 152 and the resulting mechanical coupling therebetween. Mechanistically, the beveled or chamfered pair of protrusions 158 and the flared, flexibly attached pair of tabs 146 cooperate such that each tab of the pair of tabs 146 is smoothly deflected away from the other tab of the pair of tabs 146 while disposing the first connector 132 over the second connector 152 until the pair of protrusions 158 are respectively seated in the pair of through holes 147 of the pair of tabs 146, thereby mechanically coupling the first connector 132 over the second connector 152. The combination of the flared, flexibly attached pair of tabs 146 of first-connector housing 140 and the beveled or chamfered pair of protrusions 158 of the second-connector housing 154 also facilitates mechanical decoupling and removal of the first connector 132 from the second connector 152. Mechanistically, each tab of the flared pair of tabs 146 is configured to deflect away from the other tab of the pair of tabs 146 by pulling each tab away from the other tab as shown in FIG. 6. Pulling each tab of the pair of tabs 146 away from the other tab of the pair of tabs 146, unseats the pair of protrusions 158 from the pair of through holes 147 of the pair of tabs 146, thereby mechanically decoupling the first connector 132 from the second connector 152 for removing the first connector 132 from the second connector 152.

Minor sides, or short sides, of each housing of the first-connector housing 140 and the second-connector housing 154 are dissimilar. This is best shown in FIG. 6 for the minor sides of the first-connector housing 140. Each minor side of the minor sides of the first-connector housing 140 has a matching minor side of the minor sides of the second-connector housing 154. This enforces a single orientation of the first connector 132 when disposing the first connector 132 over the second connector 152. The minor side of the first-connector housing 140 opposite the minor side including the electrical lead 134 therethrough also includes a notch 149 forming a secondary opening in the first-connector housing 140 configured to accept a fin-like extension 159 of the second-connector housing 154 when disposing the first connector 132 over the second connector 152. This further enforces a single orientation of the first connector 132 when disposing the first connector 132 over the second connector 152.

The first-connector housing 140 includes a pair of opposing finger pads 145, of which pair of finger pads 145 only one finger pad is shown in FIG. 5. The pair of finger pads 145 is configured for pushing the first connector 132 onto the second connector 152 or pulling the first connector 132 off of the second connector 152. Each finger pad of the pair of finger pads 145 includes a depression between the medial portion of the major side of the first-connector housing 140 including the finger pad and a closed end of the first-connector housing 140. As shown in FIG. 5, the closed end of the first-connector housing 140 can also include a finger pad configured for pushing the first connector 132 onto the second connector 152.

Continuing with the configuration of the first connector 132 and the second connector 152 of the connection system 100 for establishing one or more electrical connections between the first connector 132 and the second connector 152 through a sterile drape, the first piercing element 142 of one or more piercing elements within the first-connector housing 140 is configured to pierce the drape from a sterile side of the drape and insert in the first receptacle 156 of one or more receptacle within the second-connector housing 154, thereby forming at least one electrical connection of the one or more electrical connections when the first connector 132 is disposed over the second connector 152 with the drape therebetween. As set forth below, each of the first piercing element 142 and the first receptacle 156 can include more than one electrical contact. Therefore, more than one electrical connection can be formed when the first piercing element 142 is inserted in the first receptacle 156.

Beginning with an embodiment in which the first piercing element 142 is the only piercing element within the first-connector housing 140, the first piercing element 142 can be a tip-sleeve ("TS") jack plug having a needle-like tip electrical contact and a sleeve electrical contact configured to make at least two of the one or more electrical connections upon insertion of the first piercing element 142 into a complementary jack as the first receptacle 156 within the second-connector housing 154. Alternatively, the first piercing element 142 can be a tip-ring-sleeve ("TRnS") jack plug having a needle-like tip, n ring electrical contacts with n≥1 (N), and a sleeve electrical contact configured to make at least three of the one or more electrical connections upon insertion of the first piercing element 142 into a complementary jack as the first receptacle 156 within the second-connector housing 154. Each additional ring electrical contact of the first piercing element 142 when configured as a TRnS jack plug can be configured to support an additional communication channel for data transfer between the first piercing element 142 and the first receptacle 156. Regardless of whether the first piercing element 142 a TS or TRnS jack plug, the first piercing element 142 is orthogonally connected to the electrical lead 134. That is, the first piercing element 142 is at an approximately 90° angle to the electrical lead 134 extending from the first-connector housing 140 to which the first piercing element 142 is connected.

Continuing with another embodiment in which the first piercing element 142 is the only piercing element within the first-connector housing 140, the first piercing element 142 can be a blade-like end portion of a printed circuit board having the one or more electrical contacts printed thereon to make the one or more electrical connections upon insertion of the first piercing element 142 into a complementary slot as the first receptacle 156 within the second-connector housing 154. Each additional electrical contact printed on the blade-like end portion of the printed circuit board of the first piercing element 142 can be configured to support an additional communication channel for data transfer between the first piercing element 142 and the first receptacle 156. Like the TS jack plug and TRnS jack-plug embodiments of the first piercing element 142, the first piercing element 142 is also orthogonally connected to the electrical lead 134 when the first piercing element 142 is configured as a blade-like end portion of a printed circuit board. That is, the first piercing element 142 is at an approximately 90° angle to the electrical lead 134 extending from the first-connector housing 140 to which the first piercing element 142 is connected.

Continuing with the embodiment of FIGS. 5 and 6, in which the first piercing element 142 is one piercing element of a number of piercing elements, the first piercing element 142 can be accompanied by a second piercing element 141 and a third piercing element 143 within the first-connector housing 140, each piercing element of the first, second, and third piercing elements 141, 142, and 143 having one or more electrical contacts. In such embodiments, the first receptacle 156 can be accompanied by a second receptacle 155 and a third receptacle 157 within a second-connector housing 150, each receptacle of the first, second, and third receptacles 155, 156, and 157 having one or more electrical contacts complementary to the one or more electrical contacts of the first, second, and third piercing elements 141, 142, and 143 to form at least three electrical connections when the first connector 132 is disposed over the second connector 152 with the drape therebetween. Each piercing element of the first, second, and third piercing elements 142, 141, and 143 is orthogonally connected to the electrical lead 134. In addition, each piercing element of the first, second, and third piercing elements 142, 141, and 143 is configured to pierce the sterile drape in a different location than the other piercing elements.

While not shown, a drape seal can be disposed within the first connector 132 around a proximal-end portion of any one or more piercing elements of the first, second, and third piercing elements 141, 142, and 143, depending upon the embodiment. The drape seal can be a self-sealing polymeric septum configured as a sticker with a pressure-sensitive adhesive on a drape-facing side of the drape seal configured to adhere to the drape about a piercing thereof. When the first connector 132 and the second connector 152 are disconnected, the drape seal is configured to selectively pull away from the first connector 132, thereby sealing the drape.

Methods for establishing one or more electrical connections through a drape with the connection system 100 include, in some embodiments, placing the drape over the second connector 152 of the connection system 100, the second connector 152 including the second-connector housing 154 having dissimilar minor sides; aligning the first connector 132 of the connection system 100 with the second connector 152, the first connector 132 including the first-connector housing 140 having dissimilar minor sides; disposing the first connector 132 over the second connector 152 with the drape between the first connector 132 and the second connector 152, the drape self-tightening over the second connector 152 during the disposing of the first connector 132 over the second connector 152; piercing a sterile side of the drape with at least the first piercing element 142 within the first-connector housing 140 orthogonally connected to the electrical lead 134 extending from the first-connector housing 140; inserting the first piercing element 142 into at least the first receptacle 156 within the second-connector housing 154; and forming the one or more electrical connections between the first piercing element 142 of the first connector 132 and the first receptacle 156 of the second connector 152. Aligning the first connector 132 of the connection system 100 with the second connector 152 includes matching each minor side of the minor sides of the first-connector housing 140 with the matching minor side of the minor sides of the second-connector housing 154, thereby enforcing a single orientation of the first connector 132 to the second connector 152.

Disposing the first connector 132 over the second connector 152 includes inserting each protrusion of the pair of opposing protrusions 158 protruding from the medial portion of a major side of the second-connector housing 154 into a corresponding through hole of a tab of the pair of opposing tabs 146 extending from the medial portion of a major side of the first-connector housing 140.

Piercing the sterile side of the drape with the first piercing element 142 includes simultaneously piercing the sterile side of the drape in two other locations with the second piercing element 141 and the third piercing element 143 within the first-connector housing 140 orthogonally connected to the electrical lead 134 extending from the first-connector housing 140.

The methods can further include disposing the stylet in a catheter, the first connector 132 being the tether connector 132 coupled to the stylet; and sensing the location of a tip of the catheter in a patient, the second connector 152 being the fin connector 152 of the tip-location sensor 50 on a chest of the patient under the drape. Disposing the first connector 132 over the second connector 152 includes disposing the tether connector 132 over the fin connector 152 with a downward motion substantially orthogonal to the tip-location sensor.

The methods can further include disposing the first connector 132 over the second connector 152 by pushing the first connector 132 onto the second connector 152 using at least the pair of opposing finger pads 145 of the first connector 132. Each finger pad of the pair of finger pads 145 includes the depression between the medial portion of a major side of the first-connector housing 140 including the finger pad and the closed end of the first-connector housing 140.

The methods can further include sealing the drape with the drape seal disposed within the first connector 132 around at least the proximal-end portion of the first piercing element 142. When the first connector 132 and the second connector 152 are disconnected, the drape seal selectively pulls away from the first connector 132, thereby sealing the drape.

Methods can further include confirming success in forming the one or more electrical connections by a change from the first state of the LED on the first connector 132 to the second state of the LED upon forming the one or more electrical connections.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A method of establishing an electrical connection through a drape, comprising:
   positioning a sensor connector on a patient, the sensor connector including a first receptacle;
   placing the drape over the sensor connector and the patient;
   connecting a tether connector to the sensor connector through the drape, the tether connector comprising:
   a housing;
   an electrical lead extending from the housing; and
   a first piercing element in the housing orthogonally connected to the electrical lead,
   the connecting comprising piercing the drape with the first piercing element to form a first electrical connection in the first receptacle.

2. The method according to claim 1, wherein the housing of the tether connector includes an integrated clip configured to couple the tether connector to the sensor connector.

3. The method according to claim 2, wherein the integrated clip includes a pair of opposing tabs extending along opposing major sides of the tether connector.

4. The method according to claim 3, wherein the sensor connector includes a pair of opposing protrusions on opposing major sides of the sensor connector, and wherein connecting the tether connector to the sensor connector through the drape comprises pressing the integrated clip over the sensor connector until the pair of opposing protrusions are received in a pair of opposing openings in the pair of opposing tabs.

5. The method according to claim 4, wherein the pair of opposing protrusions are beveled or chamfered to facilitate reception of the pair of opposing protrusions in the pair of opposing openings in the pair of opposing tabs.

6. The method according to claim 4, wherein the pair of opposing tabs are flexibly attached to the housing of the tether connector, further comprising removing the tether connector from the sensor connector by initially deflecting the pair of opposing tabs away from the housing of the tether connector.

7. The method according to claim 1, wherein the sensor connector includes opposing minor sides differing in profile, and wherein the housing of the tether connector includes opposing minor sides matching the opposing minor sides of the sensor connector, wherein connecting the tether connector to the sensor connector through the drape further comprises aligning the opposing minor sides of the sensor connector with the opposing minor sides of the sensor connector.

8. The method according to claim 1, wherein the first piercing element is a jack plug having a needle-like tip electrical contact, one or more ring electrical contacts, and a sleeve electrical contact, and wherein the first receptacle of the sensor connector is a jack having complementary electrical contacts.

9. The method according to claim 1, wherein the sensor connector further comprises a second receptacle, wherein connecting the tether connector to the sensor connector through the drape further comprises piercing the drape with a second piercing element in the housing of the tether connector orthogonally connected to the electrical lead.

10. The method according to claim 9, wherein the sensor connector further comprises a third receptacle, wherein connecting the tether connector to the sensor connector through the drape further comprises piercing the drape with a third piercing element in the housing of the tether connector orthogonally connected to the electrical lead.

11. The method according to claim 1, wherein the housing of the tether connector includes a pair of opposing finger pads, wherein connecting the tether connector to the sensor connector through the drape further comprises gripping the housing of the tether connector such that fingers of a user are placed on the pair of opposing finger pads.

12. The method according to claim 11, wherein the housing of the tether connector includes opposing tabs configured to couple the tether connector to the sensor connector, wherein the opposing tabs are positioned in line with the pair of opposing finger pads.

13. The method according to claim 1, wherein the electrical lead is coupled to a stylet, the method further comprising inserting the stylet into a catheter, and inserting the catheter into the patient.

* * * * *